US009696564B1

(12) United States Patent
Etzkorn et al.

(10) Patent No.: US 9,696,564 B1
(45) Date of Patent: Jul. 4, 2017

(54) CONTACT LENS WITH METAL PORTION AND POLYMER LAYER HAVING INDENTATIONS

(75) Inventors: James Etzkorn, Mountain View, CA (US); Babak Amirparviz, Mountain View, CA (US); Michael Kubba, Mountain View, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 1141 days.

(21) Appl. No.: 13/590,910

(22) Filed: Aug. 21, 2012

(51) Int. Cl.
*G02C 7/00* (2006.01)
*G02C 7/04* (2006.01)
(Continued)

(52) U.S. Cl.
CPC ............ *G02C 7/04* (2013.01); *A61B 5/6821* (2013.01); *B29D 11/00817* (2013.01);
(Continued)

(58) Field of Classification Search
CPC ........ G02C 7/04; G02C 7/02; G02C 2202/16; G02C 7/049; H01L 21/56;
(Continued)

(56) References Cited

U.S. PATENT DOCUMENTS 2,129,305 A * 9/1938 Feinbloom ............ G02C 7/041
264/2.5
3,958,560 A 5/1976 March
(Continued)

FOREIGN PATENT DOCUMENTS

EP 0369942 5/1990
EP 686372 12/1995
(Continued)

OTHER PUBLICATIONS

Wall, K., "Active contact lens that lets you see like the Terminator patented," Feb. 10, 2012, http://www.patexia.com/feed/active-contact-lens-that-lets-you-see-like-the-terminator-patented-2407, Last accessed Mar. 28, 2012, 5 pages.
(Continued)

*Primary Examiner* — Patricia Mallari
*Assistant Examiner* — Karen Toth
(74) *Attorney, Agent, or Firm* — McDonnell Boehnen Hulbert & Berghoff LLP

(57) ABSTRACT

Contact lenses having embedded polymer layers, and methods for forming the same are provided. In some aspects, the contact lens can include: a substrate; a metal portion coupled to the substrate; and a polymer layer attached to the substrate and the metal portion, wherein the polymer layer has one or more indentations. The metal portion can be associated with or a part of a power supply, antenna and/or circuit in various aspects. In some aspects, the substrate can encapsulate the metal portion and the polymer layer. In some aspects, a method can include: forming a metal ring; fabricating one or more components on the metal ring; forming a polymer layer ring having indentations; providing the metal ring and the polymer layer ring in a contact lens mold; and encapsulating the contact lens mold with conventional hydrogel, silicone hydrogel, silicone elastomer, polyacrylamide, siloxane-based hydrogel or fluorosiloxane-based hydrogel.

11 Claims, 11 Drawing Sheets

(51) Int. Cl.
    *B29D 11/00*     (2006.01)
    *A61B 5/00*     (2006.01)
    *G02B 1/04*     (2006.01)
    *G02C 7/02*     (2006.01)
    *G01N 27/327*     (2006.01)
    *A61B 5/145*     (2006.01)

(52) U.S. Cl.
    CPC ...... *A61B 5/14507* (2013.01); *G01N 27/3272* (2013.01); *G02B 1/043* (2013.01); *G02C 7/02* (2013.01)

(58) Field of Classification Search
    CPC .......... B29D 11/00817; A61B 5/14507; A61B 5/6821; G01N 27/3272; G02B 1/043
    See application file for complete search history.

(56) References Cited

U.S. PATENT DOCUMENTS

| | | |
|---|---|---|
| 4,014,321 A | 3/1977 | March |
| 4,055,378 A | 10/1977 | Feneberg et al. |
| 4,122,942 A | 10/1978 | Wolfson |
| 4,136,250 A | 1/1979 | Mueller et al. |
| 4,143,949 A | 3/1979 | Chen |
| 4,153,641 A | 5/1979 | Deichert et al. |
| 4,214,014 A | 7/1980 | Hofer et al. |
| 4,309,085 A | 1/1982 | Morrison |
| 4,312,575 A | 1/1982 | Peyman et al. |
| 4,401,371 A | 8/1983 | Neefe |
| 4,463,149 A | 7/1984 | Ellis |
| 4,555,372 A | 11/1985 | Kunzler et al. |
| 4,604,479 A | 8/1986 | Ellis |
| 4,632,844 A | 12/1986 | Yanagihara et al. |
| 4,686,267 A | 8/1987 | Ellis et al. |
| 4,740,533 A | 4/1988 | Su et al. |
| 4,826,936 A | 5/1989 | Ellis |
| 4,996,275 A | 2/1991 | Ellis et al. |
| 4,997,770 A | 3/1991 | Giles et al. |
| 5,032,658 A | 7/1991 | Baron et al. |
| 5,034,461 A | 7/1991 | Lai et al. |
| 5,070,215 A | 12/1991 | Bambury et al. |
| 5,135,297 A | 8/1992 | Valint et al. |
| 5,177,165 A | 1/1993 | Valint et al. |
| 5,177,168 A | 1/1993 | Baron et al. |
| 5,219,965 A | 6/1993 | Valint et al. |
| 5,260,000 A | 11/1993 | Nandu et al. |
| 5,271,875 A | 12/1993 | Appleton et al. |
| 5,310,779 A | 5/1994 | Lai |
| 5,321,108 A | 6/1994 | Kunzler et al. |
| 5,326,584 A | 7/1994 | Kamel et al. |
| 5,336,797 A | 8/1994 | McGee et al. |
| 5,346,976 A | 9/1994 | Ellis et al. |
| 5,347,326 A * | 9/1994 | Volk ...................... A61B 3/125 351/159.02 |
| 5,358,995 A | 10/1994 | Lai et al. |
| 5,364,918 A | 11/1994 | Valint et al. |
| 5,387,662 A | 2/1995 | Kunzler et al. |
| 5,449,729 A | 9/1995 | Lai |
| 5,472,436 A | 12/1995 | Fremstad |
| 5,512,205 A | 4/1996 | Lai |
| 5,585,871 A | 12/1996 | Linden |
| 5,610,252 A | 3/1997 | Bambury et al. |
| 5,616,757 A | 4/1997 | Bambury et al. |
| 5,682,210 A | 10/1997 | Weirich |
| 5,708,094 A | 1/1998 | Lai et al. |
| 5,710,302 A | 1/1998 | Kunzler et al. |
| 5,714,557 A | 2/1998 | Kunzler et al. |
| 5,726,733 A | 3/1998 | Lai et al. |
| 5,760,100 A | 6/1998 | Nicolson et al. |
| 5,908,906 A | 6/1999 | Kunzler et al. |
| 5,981,669 A | 11/1999 | Valint et al. |
| 6,087,941 A | 7/2000 | Ferraz |
| 6,131,580 A | 10/2000 | Ratner et al. |
| 6,193,369 B1 | 2/2001 | Valint et al. |
| 6,200,626 B1 | 3/2001 | Grobe et al. |
| 6,213,604 B1 | 4/2001 | Valint et al. |
| 6,217,171 B1 * | 4/2001 | Auten ...................... A61F 2/145 351/159.02 |
| 6,312,393 B1 | 11/2001 | Abreu |
| 6,348,507 B1 | 2/2002 | Heiler et al. |
| 6,366,794 B1 | 4/2002 | Moussy et al. |
| 6,423,001 B1 | 7/2002 | Abreu |
| 6,428,839 B1 | 8/2002 | Kunzler et al. |
| 6,431,705 B1 | 8/2002 | Linden |
| 6,440,571 B1 | 8/2002 | Valint et al. |
| 6,450,642 B1 | 9/2002 | Jethmalani et al. |
| 6,532,298 B1 | 3/2003 | Cambier et al. |
| 6,550,915 B1 | 4/2003 | Grobe, III |
| 6,570,386 B2 | 5/2003 | Goldstein |
| 6,579,235 B1 | 6/2003 | Abita et al. |
| 6,599,559 B1 | 7/2003 | McGee et al. |
| 6,614,408 B1 | 9/2003 | Mann |
| 6,630,243 B2 | 10/2003 | Valint et al. |
| 6,638,563 B2 | 10/2003 | McGee et al. |
| 6,726,322 B2 | 4/2004 | Andino et al. |
| 6,735,328 B1 | 5/2004 | Helbing et al. |
| 6,779,888 B2 | 8/2004 | Marmo |
| 6,804,560 B2 | 10/2004 | Nisch et al. |
| 6,851,805 B2 | 2/2005 | Blum et al. |
| 6,885,818 B2 | 4/2005 | Goldstein |
| 6,939,299 B1 | 9/2005 | Petersen et al. |
| 6,980,842 B2 | 12/2005 | March et al. |
| 7,018,040 B2 | 3/2006 | Blum et al. |
| 7,131,945 B2 | 11/2006 | Fink et al. |
| 7,169,106 B2 | 1/2007 | Fleischman et al. |
| 7,398,119 B2 | 7/2008 | Lambert et al. |
| 7,423,801 B2 | 9/2008 | Kaufman et al. |
| 7,429,465 B2 | 9/2008 | Muller et al. |
| 7,441,892 B2 | 10/2008 | Hsu |
| 7,443,016 B2 | 10/2008 | Tsai et al. |
| 7,450,981 B2 | 11/2008 | Jeon |
| 7,639,845 B2 | 12/2009 | Utsunomiya |
| 7,654,671 B2 | 2/2010 | Glynn |
| 7,699,465 B2 | 4/2010 | Dootjes et al. |
| 7,728,949 B2 | 6/2010 | Clarke et al. |
| 7,751,896 B2 | 7/2010 | Graf et al. |
| 7,799,243 B2 | 9/2010 | Mather et al. |
| 7,809,417 B2 | 10/2010 | Abreu |
| 7,878,650 B2 | 2/2011 | Fritsch et al. |
| 7,885,698 B2 | 2/2011 | Feldman |
| 7,907,931 B2 | 3/2011 | Hartigan et al. |
| 7,926,940 B2 | 4/2011 | Blum et al. |
| 7,931,832 B2 | 4/2011 | Pugh et al. |
| 7,964,390 B2 | 6/2011 | Rozakis et al. |
| 8,080,187 B2 | 12/2011 | Tepedino, Jr. et al. |
| 8,096,654 B2 | 1/2012 | Amirparviz et al. |
| 8,118,752 B2 | 2/2012 | Hetling et al. |
| 8,142,016 B2 | 3/2012 | Legerton et al. |
| 8,224,415 B2 | 7/2012 | Budiman |
| 8,742,623 B1 | 6/2014 | Biederman et al. |
| 8,764,185 B1 | 7/2014 | Biederman et al. |
| 8,798,332 B2 | 8/2014 | Otis et al. |
| 8,820,934 B1 | 9/2014 | Ho et al. |
| 8,821,811 B2 | 9/2014 | Liu et al. |
| 8,827,445 B1 | 9/2014 | Wiser et al. |
| 8,833,934 B1 | 9/2014 | Wiser et al. |
| 8,857,981 B2 | 10/2014 | Pletcher et al. |
| 8,864,305 B2 | 10/2014 | Pletcher et al. |
| 8,870,370 B1 | 10/2014 | Otis et al. |
| 8,874,182 B2 * | 10/2014 | Etzkorn ............. A61B 5/14532 204/403.01 |
| 8,880,139 B1 * | 11/2014 | Etzkorn ............. G01N 27/3271 204/403.01 |
| 8,881,892 B1 | 11/2014 | Linhardt et al. |
| 8,886,275 B2 * | 11/2014 | Etzkorn ............. A61B 5/14532 204/403.01 |
| 8,909,311 B2 | 12/2014 | Ho et al. |
| 8,919,953 B1 | 12/2014 | Ho |
| 8,922,366 B1 | 12/2014 | Honore et al. |
| 8,926,809 B2 | 1/2015 | Pletcher et al. |
| 8,950,068 B2 | 2/2015 | Etzkorn |
| 8,960,898 B1 | 2/2015 | Etzkorn et al. |

(56) References Cited

U.S. PATENT DOCUMENTS

| | | |
|---|---|---|
| 8,960,899 B2 * | 2/2015 | Etzkorn ............... G02C 7/049 351/159.03 |
| 8,965,478 B2 | 2/2015 | Liu |
| 8,971,978 B2 | 3/2015 | Ho et al. |
| 8,979,271 B2 | 3/2015 | Pletcher et al. |
| 8,985,763 B1 | 3/2015 | Etzkorn et al. |
| 8,989,834 B2 | 3/2015 | Ho et al. |
| 9,009,958 B2 | 4/2015 | Etzkorn |
| 9,024,727 B1 | 5/2015 | Otis et al. |
| 9,028,772 B2 | 5/2015 | Yao et al. |
| 9,030,239 B1 | 5/2015 | Dastgheib et al. |
| 9,044,075 B2 | 6/2015 | Linhardt et al. |
| 9,044,200 B1 | 6/2015 | Liu et al. |
| 9,047,512 B2 | 6/2015 | Otis et al. |
| 9,054,079 B2 * | 6/2015 | Etzkorn ............... G02C 7/049 351/159.03 |
| 9,055,902 B2 | 6/2015 | Liu |
| 9,063,351 B1 | 6/2015 | Ho et al. |
| 9,084,561 B2 * | 7/2015 | Etzkorn ............ G01N 27/3271 |
| 9,095,312 B2 | 8/2015 | Yao et al. |
| 9,101,309 B1 | 8/2015 | Liu et al. |
| 9,111,473 B1 | 8/2015 | Ho et al. |
| 9,113,829 B2 | 8/2015 | Etzkorn |
| 9,128,305 B2 | 9/2015 | Honore et al. |
| 9,158,133 B1 | 10/2015 | Pletcher et al. |
| 9,161,712 B2 | 10/2015 | Etzkorn |
| 9,176,332 B1 | 11/2015 | Etzkorn et al. |
| 9,184,698 B1 | 11/2015 | Wiser et al. |
| 9,251,455 B2 | 2/2016 | Lin et al. |
| 2002/0193674 A1 | 12/2002 | Fleischman et al. |
| 2003/0179094 A1 | 9/2003 | Abreu |
| 2004/0027536 A1 | 2/2004 | Blum et al. |
| 2004/0116794 A1 | 6/2004 | Fink et al. |
| 2005/0045589 A1 | 3/2005 | Rastogi et al. |
| 2005/0221276 A1 | 10/2005 | Rozakis et al. |
| 2007/0016074 A1 | 1/2007 | Abreu |
| 2007/0030443 A1 | 2/2007 | Chapoy et al. |
| 2007/0121065 A1 | 5/2007 | Cox et al. |
| 2007/0188710 A1 | 8/2007 | Hetling et al. |
| 2008/0002149 A1 * | 1/2008 | Fritsch ................. G02C 7/04 351/159.02 |
| 2008/0208335 A1 | 8/2008 | Blum et al. |
| 2008/0218696 A1 | 9/2008 | Mir |
| 2009/0033863 A1 | 2/2009 | Blum et al. |
| 2009/0036761 A1 | 2/2009 | Abreu |
| 2009/0057164 A1 | 3/2009 | Minick et al. |
| 2009/0076367 A1 | 3/2009 | Sit et al. |
| 2009/0118604 A1 | 5/2009 | Phan et al. |
| 2009/0189830 A1 | 7/2009 | Deering et al. |
| 2009/0196460 A1 | 8/2009 | Jakobs et al. |
| 2010/0001926 A1 | 1/2010 | Amirparviz et al. |
| 2010/0013114 A1 | 1/2010 | Bowers et al. |
| 2010/0016704 A1 | 1/2010 | Naber et al. |
| 2010/0028559 A1 | 2/2010 | Yan et al. |
| 2010/0036488 A1 | 2/2010 | de Juan et al. |
| 2010/0072643 A1 | 3/2010 | Pugh et al. |
| 2010/0103368 A1 * | 4/2010 | Amirparviz ...... B29D 11/00826 351/158 |
| 2010/0109175 A1 | 5/2010 | Pugh et al. |
| 2010/0110372 A1 | 5/2010 | Pugh et al. |
| 2010/0113901 A1 | 5/2010 | Zhang et al. |
| 2010/0133510 A1 | 6/2010 | Kim et al. |
| 2010/0249548 A1 | 9/2010 | Muller |
| 2011/0015512 A1 | 1/2011 | Pan et al. |
| 2011/0028807 A1 | 2/2011 | Abreu |
| 2011/0040161 A1 | 2/2011 | Abreu |
| 2011/0055317 A1 | 3/2011 | Vonog et al. |
| 2011/0063568 A1 | 3/2011 | Meng et al. |
| 2011/0084834 A1 | 4/2011 | Sabeta |
| 2011/0116035 A1 | 5/2011 | Fritsch et al. |
| 2011/0157541 A1 | 6/2011 | Peyman |
| 2011/0157544 A1 | 6/2011 | Pugh et al. |
| 2011/0184271 A1 | 7/2011 | Veciana et al. |
| 2011/0274680 A1 | 11/2011 | Mazed et al. |
| 2011/0286064 A1 | 11/2011 | Burles et al. |
| 2011/0298794 A1 | 12/2011 | Freedman |
| 2012/0026458 A1 | 2/2012 | Qiu et al. |
| 2012/0038881 A1 | 2/2012 | Amirparviz et al. |
| 2012/0041287 A1 | 2/2012 | Goodall et al. |
| 2012/0041552 A1 | 2/2012 | Chuck et al. |
| 2012/0069254 A1 | 3/2012 | Burton |
| 2012/0075168 A1 | 3/2012 | Osterhout et al. |
| 2012/0075574 A1 | 3/2012 | Pugh et al. |
| 2012/0078071 A1 | 3/2012 | Bohm et al. |
| 2012/0088258 A1 | 4/2012 | Bishop et al. |
| 2012/0092612 A1 | 4/2012 | Binder |
| 2012/0109296 A1 | 5/2012 | Fan |
| 2012/0177576 A1 | 7/2012 | Hu |
| 2012/0201755 A1 | 8/2012 | Rozakis et al. |
| 2012/0245444 A1 | 9/2012 | Otis et al. |
| 2012/0259188 A1 | 10/2012 | Besling |
| 2013/0215375 A1 * | 8/2013 | Belden ................. G02C 7/021 351/159.02 |
| 2013/0215377 A1 * | 8/2013 | Pugh ................ B29D 11/00817 351/159.39 |
| 2013/0215378 A1 * | 8/2013 | Pugh ................ B29D 11/00817 351/159.39 |
| 2014/0081178 A1 | 3/2014 | Pletcher et al. |
| 2014/0084489 A1 * | 3/2014 | Etzkorn ............... G02C 7/049 257/778 |
| 2014/0085599 A1 | 3/2014 | Etzkorn |
| 2014/0085601 A1 | 3/2014 | Etzkorn |
| 2014/0088372 A1 | 3/2014 | Saeedi et al. |
| 2014/0088381 A1 | 3/2014 | Etzkorn et al. |
| 2014/0088881 A1 | 3/2014 | Saeedi et al. |
| 2014/0098226 A1 | 4/2014 | Pletcher et al. |
| 2014/0107447 A1 | 4/2014 | Liu et al. |
| 2014/0107448 A1 | 4/2014 | Liu et al. |
| 2014/0190839 A1 | 7/2014 | Liu |
| 2014/0192311 A1 | 7/2014 | Pletcher et al. |
| 2014/0192315 A1 | 7/2014 | Liu et al. |
| 2014/0194706 A1 | 7/2014 | Liu et al. |
| 2014/0197558 A1 | 7/2014 | Linhardt et al. |
| 2014/0206966 A1 | 7/2014 | Liu et al. |
| 2014/0209481 A1 | 7/2014 | Pletcher et al. |
| 2014/0329303 A1 | 11/2014 | Liu et al. |
| 2014/0371559 A1 | 12/2014 | Etzkorn et al. |
| 2014/0371560 A1 | 12/2014 | Etzkorn et al. |
| 2015/0002270 A1 | 1/2015 | Otis et al. |
| 2015/0005597 A1 | 1/2015 | Wiser et al. |
| 2015/0005602 A1 | 1/2015 | Linhardt et al. |
| 2015/0005604 A1 | 1/2015 | Biederman et al. |
| 2015/0038809 A1 | 2/2015 | Etzkorn et al. |
| 2015/0061837 A1 | 3/2015 | Honore et al. |
| 2015/0065820 A1 | 3/2015 | Ho et al. |
| 2015/0076909 A1 | 3/2015 | Biederman et al. |
| 2015/0112175 A1 | 4/2015 | Yao et al. |
| 2015/0148647 A1 | 5/2015 | Liu et al. |
| 2015/0148774 A1 | 5/2015 | Yao |
| 2015/0159190 A1 | 6/2015 | Liu |
| 2015/0160151 A1 | 6/2015 | Liu et al. |
| 2015/0164321 A1 | 6/2015 | Weibel et al. |
| 2015/0170504 A1 | 6/2015 | Jooste |
| 2015/0173474 A1 | 6/2015 | Barrows et al. |
| 2015/0173602 A1 | 6/2015 | Barrows et al. |
| 2015/0173658 A1 | 6/2015 | Liu et al. |
| 2015/0173680 A1 | 6/2015 | Etzkorn et al. |
| 2015/0182116 A1 | 7/2015 | Pletcher et al. |
| 2015/0183173 A1 | 7/2015 | Linhardt et al. |
| 2015/0186701 A1 | 7/2015 | Otis et al. |
| 2015/0186702 A1 | 7/2015 | Pletcher et al. |
| 2015/0188197 A1 | 7/2015 | Liu et al. |
| 2015/0188607 A1 | 7/2015 | Pletcher et al. |
| 2015/0212340 A1 | 7/2015 | Etzkorn |
| 2015/0214567 A1 | 7/2015 | Etzkorn et al. |
| 2015/0226692 A1 | 8/2015 | Dastgheib et al. |
| 2015/0362749 A1 | 12/2015 | Biederman et al. |
| 2015/0362750 A1 | 12/2015 | Yeager et al. |
| 2015/0362751 A1 | 12/2015 | Biederman |
| 2015/0362752 A1 | 12/2015 | Linhardt et al. |
| 2015/0362753 A1 | 12/2015 | Pletcher et al. |
| 2015/0362754 A1 | 12/2015 | Etzkorn et al. |
| 2015/0362755 A1 | 12/2015 | Lee et al. |
| 2015/0362756 A1 | 12/2015 | Wiser et al. |

(56) References Cited

U.S. PATENT DOCUMENTS

| | | | |
|---|---|---|---|
| 2015/0363280 | A1 | 12/2015 | Yeager et al. |
| 2015/0363614 | A1 | 12/2015 | Yeager et al. |
| 2015/0363617 | A1 | 12/2015 | Honore |
| 2015/0364822 | A1 | 12/2015 | O'Driscoll |
| 2016/0003760 | A1 | 1/2016 | Etzkorn |
| 2016/0006115 | A1 | 1/2016 | Etzkorn |

FOREIGN PATENT DOCUMENTS

| | | | |
|---|---|---|---|
| EP | 1061874 | 12/2000 | |
| EP | 1617757 | 1/2006 | |
| EP | 1818008 | 8/2007 | |
| EP | 1947501 | 7/2008 | |
| EP | 2457122 | 5/2012 | |
| WO | 95/04609 | 2/1995 | |
| WO | 0116641 | 3/2001 | |
| WO | 01/34312 | 5/2001 | |
| WO | 03065876 | 8/2003 | |
| WO | 2004/060431 | 7/2004 | |
| WO | 2004064629 | 8/2004 | |
| WO | 2006015315 | 2/2006 | |
| WO | 2009094643 | 7/2009 | |
| WO | 2010105728 | 9/2010 | |
| WO | 2010133317 | 11/2010 | |
| WO | 2011/011344 | 1/2011 | |
| WO | 2011034592 | 3/2011 | |
| WO | 2011035228 | 3/2011 | |
| WO | 2011035262 | 3/2011 | |
| WO | 2011083105 | 7/2011 | |
| WO | 2011163080 | 12/2011 | |
| WO | 2012035429 | 3/2012 | |
| WO | 2012037455 | 3/2012 | |
| WO | 2012051167 | 4/2012 | |
| WO | 2012051223 | 4/2012 | |
| WO | 2012052765 | 4/2012 | |
| WO | WO 2012/052765 | * 4/2012 | ............... A61B 3/16 |

OTHER PUBLICATIONS

Parviz, Babak A., "Augmented Reality in a Contact Lens," IEEE Spectrum, Sep. 2009, http://spectrum.ieee.org/biomedical/bionics/augmented-reality-in-a-contact-lens/0, Last accessed Mar. 14, 2012, 6 pages.

Bionic contact lens 'To project emails before eyes,' http://www.kurzweilai.net/forums/topic/bionic-contact-lens-to-project-emails-before-eyes, Last accessed Mar. 14, 2012, 2 pages.

Tweedie, et al., "Contact creep compliance of viscoelastic materials via nanoindentation," J. Mater. Res., Jun. 2006, vol. 21, No. 2, pp. 1576-1589, Materials Research Society.

Brahim, et al., "Polypyrrole-hydrogel composites for the construction of clinically important biosensors," 2002, Biosensors & Bioelectronics, vol. 17, pp. 53-59.

Huang, et al., "Wrinkling of Ultrathin Polymer Films," Mater. Res. Soc. Symp. Proc., 2006, vol. 924, 6 pages, Materials Research Society.

Zarbin, et al., "Nanotechnology in ophthalmology," Can J Ophthalmol, 2010, vol. 45, No. 5, pp. 457-476.

Selner, et al., "Novel Contact Lens Electrode Array for Multi-electrode Electroretinography (meERG)," IEEE, 2011, 2 pages.

Liao, et al., "A 3-µW CMOS Glucose Sensor for Wireless Contact-Lens Tear Glucose Monitoring," IEEE Journal of Solid-State Circuits, Jan. 2012, vol. 47, No. 1, pp. 335-344.

Chen, et al., "Microfabricated Implantable Parylene-Based Wireless Passive Intraocular Pressure Sensors," Journal of Microelectromechanical Systems, Dec. 2008, vol. 17, No. 6, pp. 1342-1351.

Thomas, et al., "Functional Contact Lenses for Remote Health Monitoring in Developing Countries," IEEE Global Humanitarian Technology Conference, 2011, pp. 212-217, IEEE Computer Society.

Pandey, et al., "A Fully Integrated RF-Powered Contact Lens With a Single Element Display," IEEE Transactions On Biomedical Circuits and Systems, Dec. 2010, vol. 4, No. 6, pages.

Lingley, et al., "Multipurpose integrated active contact lenses," SPIE, 2009, 2 pages.

Chu, et al., "Soft Contact-lens Sensor for Monitoring Tear Sugar as Novel Wearable Device of Body Sensor Network," http://www.ksi.edu/seke/dms11/DMS/2_Kohji_Mitsubayashi.pdf, Last accessed Jul. 27, 2012, 4 pages.

Liao, et al., "A 3µW Wirelessly Powered CMOS Glucose Sensor for an Active Contact Lens," 2011 IEEE International Solid-State Circuits Conference, Session 2, Feb. 21, 2011, 3 pages.

Hurst, "How contact lenses could help save your life," Mail Online, Apr. 19, 2010, http://www.dailymail.co.uk/health/article-1267345/How-contact-lenses-help-save-life.html, Last accessed Jul. 27, 2012.

Lončar, et al., "Design and Fabrication of Silicon Photonic Crystal Optical Waveguides," Journal of Lightwave Technology, Oct. 2000, vol. 18, No. 10, pp. 1402-1411.

Liu, et al., "Miniature Amperometric Self-Powered Continuous Glucose Sensor with Linear Response," Analytical Chemistry, 7 pages.

Baxter, "Capacitive Sensors," 2000, 17 pages.

Lingley, et al., "A Single-Pixel Wireless Contact Lens Display," Journal of Micromechanics and Microengineering, 2011, 9 pages.

"Polyvinylidene fluoride," Wikipedia, http://en.wikipedia.org/wiki/Polyvinylidene_fluoride, Last accessed Mar. 30, 2012, 4 pages.

Murdan, "Electro-responsive drug delivery from hydrogels," Journal of Controlled Release, 2003, vol. 92, pp. 1-17.

Haders, "New Controlled Release Technologies Broaden Opportunities for Ophthalmic Therapies," Drug Delivery Technology, Jul./Aug. 2009, vol. 8, No. 7, pp. 48-53.

Singh, et al., "Novel Approaches in Formulation and Drug Delivery using Contact Lenses," Journal of Basic and Clinical Pharmacy, May 2011, vol. 2, Issue 2, pp. 87-101.

"Contact Lenses: Look Into My Eyes," The Economist, Jun. 2, 2011, http://www.economist.com/node/18750624/print, Last accessed Mar. 13, 2012, 8 pages.

Holloway, "Microsoft developing electronic contact lens to monitor blood sugar," Gizmag, Jan. 5, 2012, http://www.gizmag.com/microsoft-electronic-diabetic-contact-lens/20987/, Last accessed Mar. 13, 2012, 5 pages.

Badugu et al., "A Glucose Sensing Contact Lens: A Non-Invasive Technique for Continuous Physiological Glucose Monitoring," Journal of Fluorescence, Sep. 2003, pp. 371-374, vol. 13, No. 5.

Carlson et al., "A 20 mV Input Boost Converter With Efficient Digital Control for Thermoelectric Energy Harvesting," IEEE Journal of Solid-State Circuits, Apr. 2010, pp. 741-750, vol. 45, No. 4.

Chu et al., "Biomedical soft contact-lens sensor for in situ ocular biomonitoring of tear contents," Biomed Microdevices, 2011, pp. 603-611, vol. 13.

Chu et al., "Soft contact lens biosensor for in situ monitoring of tear glucose as non-invasive blood sugar assessment," Talanta, 2011, pp. 960-965, vol. 83.

Ho et al., "Contact Lens With Integrated Inorganic Semiconductor Devices," MEMS 2008. IEEE 21st International Conference on. IEEE, 2008., pp. 403-406.

Lähdesmäki et al., "Possibilities for Continuous Glucose Monitoring by a Functional Contact Lens," IEEE Instrumentation & Measurement Magazine, Jun. 2010, pp. 14-17.

Lingley et al., "A contact lens with integrated micro solar cells," Microsyst Technol, 2012, pp. 453-458, vol. 18.

Parviz, Babak A., "For Your Eyes Only," IEEE Spectrum, Sep. 2009, pp. 36-41.

Saeedi, E. et al., "Self-assembled crystalline semiconductor optoelectronics on glass and plastic," J. Micromech. Microeng., 2008, pp. 1-7, vol. 18.

Saeedi et al., "Self-Assembled Inorganic Micro-Display on Plastic," Micro Electro Mechanical Systems, 2007. MEMS. IEEE 20th International Conference on. IEEE, 2007., pp. 755-758.

Sensimed Triggerfish, Sensimed Brochure, 2010, 10 pages.

Shih, Yi-Chun et al., "An Inductorless DC-DC Converter for Energy Harvesting With a 1.2-µW Bandgap-Referenced Output Controller,"

(56) References Cited

OTHER PUBLICATIONS

IEEE Transactions on Circuits and Systems—II: Express Briefs, Dec. 2011, pp. 832-836, vol. 58, No. 12.

Shum et al., "Functional modular contact lens," Proc. of SPIE, 2009, pp. 73970K-1 to 73970K-8, vol. 7397.

Stauth et al., "Self-assembled single-crystal silicon circuits on plastic," PNAS, Sep. 19, 2006, pp. 13922-13927, vol. 103, No. 38.

Yao, H. et al., "A contact lens with integrated telecommunication circuit and sensors for wireless and continuous tear glucose monitoring," J. Micromech. Microeng., 2012, pp. 1-10, vol. 22.

Yao, H. et al., "A Dual Microscal Glucose Sensor on a Contact Lens, Tested in Conditions Mimicking the Eye," Micro Electro Mechanical Systems (MEMS), 2011 IEEE 24th International Conference on. IEEE, 2011, pp. 25-28.

Yao et al., "A contact lens with embedded sensor for monitoring tear glucose level," Biosensors and Bioelectronics, 2011, pp. 3290-3296, vol. 26.

Yao, H. et al., "A Soft Hydrogel Contact Lens with an Encapsulated Sensor for Tear Glucose Monitoring," Micro Electro Mechanical Systems (MEMS), 2012 IEEE 25th International Conference on. IEEE, 2012, pp. 769-772.

Yeager et al., "A 9 μA, Addressable Gen2 Sensor Tag for Biosignal Acquistion," IEEE Journal of Solid-State Circuits, Oct. 2010, pp. 2198-2209, vol. 45, No. 10.

Zhang et al., "Design for Ultra-Low Power Biopotential Amplifiers for Biosignal Acquistion Applications," IEEE Transactions on Biomedical Circuits and Systems, 2012, pp. 344-355, vol. 6, No. 4.

\* cited by examiner

CONTACT LENS WITH METAL PORTION AND POLYMER LAYER HAVING INDENTATIONS

TECHNICAL FIELD

This disclosure generally relates to a contact lens with a metal portion and a polymer layer having indentations.

BACKGROUND

Thermoforming involves the application of heat and/or pressure to change shape of a polymer. When a polymer is molded from a straight shape to a non-straight shape, wrinkling can occur. Accordingly, apparatus and methods for mitigating polymer wrinkling are desired.

DETAILED DESCRIPTION

Figure 1A:
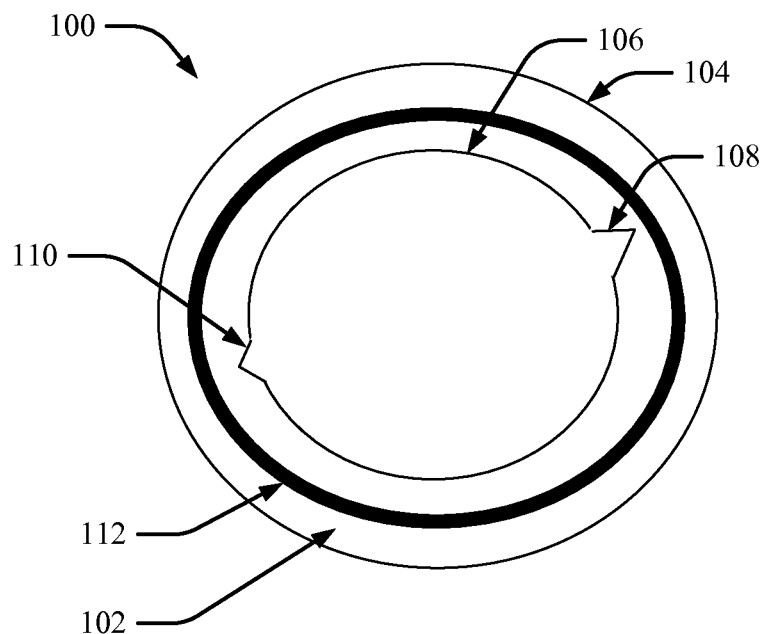
FIGS. 1A, 1B, 1C, 1D, 1E, 1F and 1G are illustrations of diagrams of exemplary non-limiting contact lenses with a metal portion and attached polymer layer with indentations that reduce a likelihood of wrinkling of the polymer layer in accordance with aspects described herein.

Various aspects are now described with reference to the drawings, wherein like reference numerals are used to refer to like elements throughout. In the following description, for purposes of explanation, numerous specific details are set forth in order to provide a more thorough understanding of one or more aspects. It is be evident, however, that such aspects can be practiced without these specific details. In other instances, structures and devices are shown in block diagram form in order to facilitate describing one or more aspects.

As used in this application, the terms "component," "component," "system," and the like are intended to refer to a computer-related entity, either hardware, software, firmware, a combination of hardware and software, software and/or software in execution. For example, a component can be, but is not limited to being, a process running on a processor, a processor, an object, an executable, a thread of execution, a program, and/or a computer. By way of illustration, both an application running on a computing device and/or the computing device can be a component. In addition, components can execute from various computer-readable storage media having various data structures stored thereon. The components can communicate by way of local and/or remote processes such as in accordance with a signal having one or more data packets (e.g., data from one component interacting with another component in a local system, distributed system, and/or across a network such as the Internet with other systems by way of the signal).

The word "exemplary" is used herein to mean serving as an example, instance, or illustration. For the avoidance of doubt, the subject matter disclosed herein is not limited by such examples. In addition, any aspect or design described in this disclosure as "exemplary" is not necessarily to be construed as preferred or advantageous over other aspects or designs, nor is it meant to preclude equivalent exemplary structures and techniques known to those of ordinary skill in the art. Furthermore, to the extent that the terms "includes," "has," "contains," and other similar words are used in either the detailed description or the claims, for the avoidance of doubt, such terms are intended to be inclusive in a manner similar to the term "comprising" as an open transition word without precluding any additional or other elements.

For an elastic film (e.g., on an elastic substrate), a critical compressive stress exists, beyond which an equilibrium wrinkled state can be determined from an energetic analysis that accounts for elastic strain energy in the film and in the substrate. Surface energy is considered negligible in conventional analysis. However, as film thickness reduces (e.g., reaches the nanometer (nm) scale), surface energy as well as other surface effects can become important. For ultrathin polymer films (e.g., thickness less than 30 nm), measured wrinkle wavelengths can deviate from conventional solutions, and deduced elastic modulus can decrease with decreasing film thickness. In addition, measured wrinkle amplitudes can also differ significantly from the conventional analysis. Accordingly, there can be a thickness-dependence associated with deduced elastic modulus in the ultrathin films. Wrinkling can relax compression-induced strain energy in the film, but also can lead to an increase in bending energy in film and strain energy in the substrate.

Such wrinkling in films is undesirable for a number of reasons. For example, wrinkling can lead to reduced clarity for the wearer of the contact lens. Furthermore, wrinkling can lead to an increased possibility for tears, discomfort and/or irritation.

Additionally, placing metal portions (e.g., portions including circuits and/or antennas) on or embedding metal portions within a substrate of a contact lens, can increase the shear stress on the substrate. As a result, the probability of wrinkling and tears, and the corresponding discomfort, lack of clarity and/or irritation is increased. Further, in some cases, wrinkling can be so severe that the metal portions do not lie flat on the substrate. Performance of circuitry, antennas or other operational components can thus be affected in these cases.

Formation of indentations (or other forms of film stress reliefs) in the polymer layer can mitigate wrinkling of the polymer layer. Selective employment of indentations in the polymer film can facilitate load balancing and/or promote linearity of forces that mitigate wrinkling or creep associated with the polymer film. Accordingly, the number and/or respective shapes of indentations utilized can be tailored to mitigate wrinkling or creep of the polymer film, for example, as a function of the thickness, surface area, shape, substrate, and type of polymer film.

Apparatus, systems and methods disclosed herein relate to contact lenses. In various aspects, the contact lenses can include a substrate, and a metal portion coupled to or disposed within the substrate. The contact lens can also include a polymer layer disposed on or within the substrate and attached to the metal portion. In various aspects, the polymer layer can have one or more indentations. The indentations can be stress relief cuts in various aspects. The indentations can be on the inner edge of the polymer layer and/or on the outer edge of the polymer layer. In some aspects, the indentations are enclosed completely within the polymer layer.

In one or more other aspects, the disclosed subject matter relates to another contact lens. The contact lens can include a polymer layer having one or more stress relief cuts on an inner edge and an outer edge of the polymer layer.

In one or more other aspects, the disclosed subject matter relates to a method of manufacturing a contact lens having a polymer layer with one or more indentations. The method can include forming a metal ring; fabricating one or more components on the metal ring; and forming a polymer layer ring having one or more indentations. In various aspects, the indentations and/or ring can be formed by removing portions of the polymer layer via an etching process. For example, reactive ion etching can be performed by applying plasma to the polymer layer. In other aspects, the indentations and/or ring can be formed by removing portions of the polymer layer via laser cutting the portions away from the polymer layer. In other aspects, the indentations and/or ring can be formed by removing portions of the polymer layer by applying a metal die in the shape of the ring or being shaped in a manner corresponding to the desired shape and location of the indentations of the polymer layer.

The method can also include providing the metal ring and the polymer layer ring in a contact lens mold. In some aspects, the metal ring and polymer layer can be formed in a curved shape corresponding to the contact lens mold prior to placing the metal ring and polymer layer ring in the contact lens mold. The method can also include encapsulating the contact lens mold with at least one of conventional hydrogel, silicone hydrogel, silicone elastomer, polyacrylamide, siloxane-based hydrogel or fluorosiloxane-based hydrogel.

The contact lenses described herein can advantageously reduce likelihood of the polymer layer wrinkling when the polymer layer experiences pressure and/or heat (e.g., during the application of the polymer layer to the metal portion). Accordingly, various drawbacks of wrinkling (e.g., lack of clarity, irritation and/or discomfort) can be minimized.

FIGS. 1A, 1B, 1C, 1D, 1E, 1F and 1G are illustrations of exemplary non-limiting contact lenses with a metal portion and attached polymer layer with indentations that reduce likelihood of wrinkling of the polymer layer in accordance with aspects described herein.

Turning first to FIG. 1A, contact lens 200 can include a polymer layer 102 having an outer edge 104 and an inner edge 106, a metal portion 112 and a substrate (not shown).

The polymer layer 102 can be disposed on or within the substrate of the contact lens 200. In some aspects, the polymer layer 102 can be integrally formed with the substrate. In various aspects, the polymer layer 102 can be substantially rigid when formed and/or substantially rigid when attached to the metal portion 112.

The polymer layer 102 can include any number of different types of polymers that are biocompatible. By way of example, but not limitation, biocompatible polymers can include numerous different materials employed in soft contact lens manufacturing including, but not limited to, conventional hydrogels, silicone hydrogels, silicone elastomers, polyacrylamide, siloxane-based hydrogel and/or fluorosiloxane-based hydrogel.

Soft contact lenses have generally been broadly grouped into two classes of materials. Conventional hydrogels are crosslinked hydrogels including hydrophilic monomers (e.g., N-vinyl pyrrolidone (NVP), N-dimethylacrylamide (DMA), hydroxyethyl methacrylate (HEMA), 2-Hydroxyethyl acrylate (HEA), methacrylic acid and acrylic acid), strengthening agents, ultraviolet (UV) blockers, and tints. Silicone hydrogels are crosslinked hydrogels that contain silicone containing macromers and monomers, as well as hydrophilic monomers that absorb water.

Turning back to FIG. 1A, the polymer layer 102 can have one or more indentations 108, 110 on the outer edge 104 and/or the inner edge 106. The one or more indentations 108, 110 can be formed in the polymer layer 102 to reduce likelihood of the polymer layer 102 wrinkling when the polymer layer 102 is bent and/or when heat or pressure is applied to the polymer layer.

The one or more indentations can be formed in the polymer layer 102 in a number of different ways. For example, a laser cutter can be employed. In these embodiments, the laser cutter can cut the circular (or, in some aspects, ring) shape of the polymer layer 102, and cut one or more of the indentations of the polymer layer 102. In some aspects, a mold having the outline of the shape of the indentations (or ring) can be placed over the polymer layer 102 prior to cutting. Different shapes and/or locations of the indentations can be cut into the polymer layer 102.

As another example, the polymer layer 102 and/or one or more indentations can be die cut. For example, to cut a ring-shaped polymer layer 102, the die can be composed of a cylinder metal component that can pierce the polymer layer 102 creating a hole through the center region of the polymer layer 102. Similarly, the die can be formed in the shape of and located at the desired positions of the one or more indentations. The die can pierce the polymer layer 102 at the locations of the desired one or more indentations and create the one or more indentations in the polymer layer 102. In various aspects, the die can be formed with different shapes along the edge of the die to enable different shapes of the indentations to be formed.

As another example, the ring shape of the polymer layer 102 and/or the one or more indentations can be removed through an etching process. For example, masking can be performed over areas of the polymer layer that will not be removed from the polymer layer 102. In some aspects, the areas of the polymer layer 102 can be masked with metal. The mask can be formed in any number of different shapes corresponding to the locations and shapes of the ring and/or indentations. The etching material can then be applied to the unmasked portions of the polymer layer 102 to remove the portion of the polymer layer 102 that is unmasked. In some embodiments, reactive ion etching (RIE) using a plasma can be employed.

The one or more indentations can be any number of different configurations and/or can have any number of different positions. Various non-limiting example configurations and/or positioning of the indentations can be appreciated with reference to FIGS. 1A, 1B, 1C, 1D, 1E, 1F and 1G.

Figure 1B:
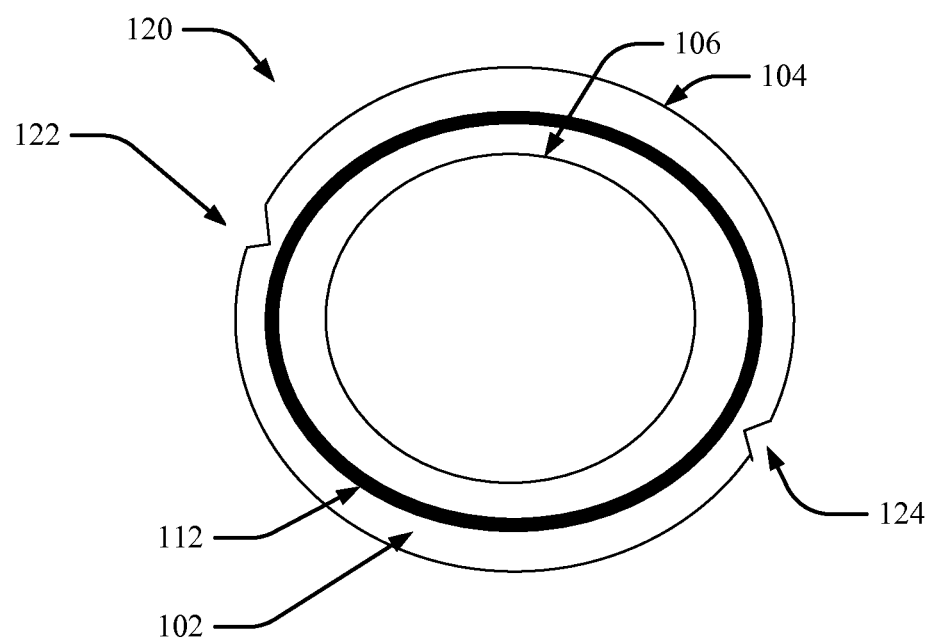
Figure 1C:
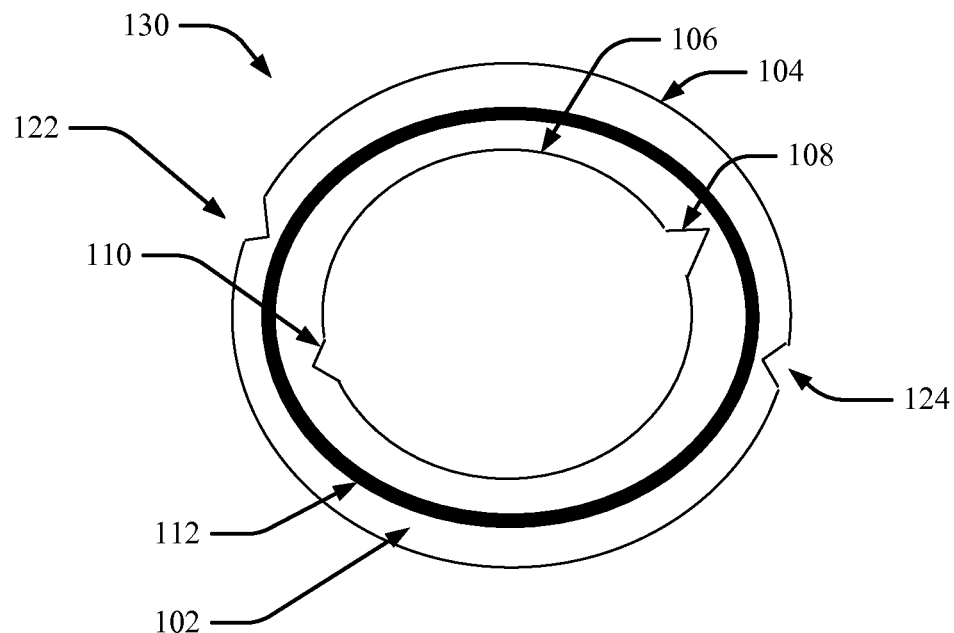
Figure 1D:
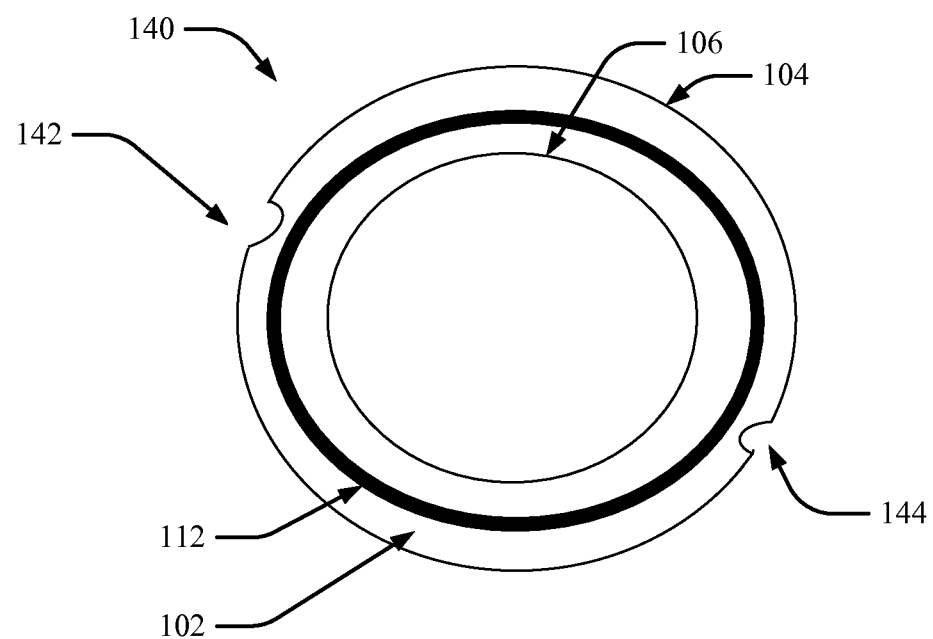
Figure 1E:
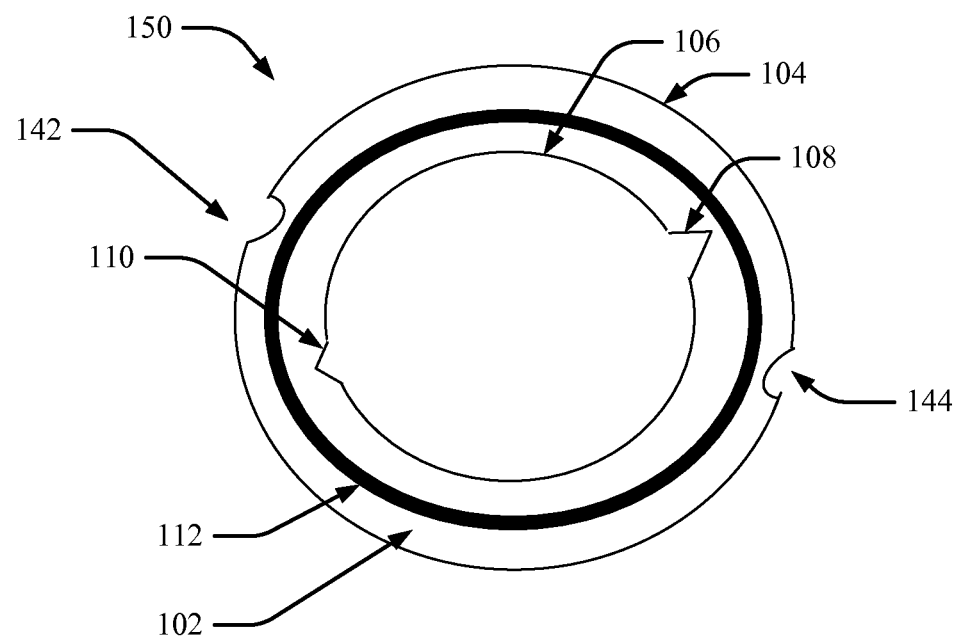
Figure 1F:
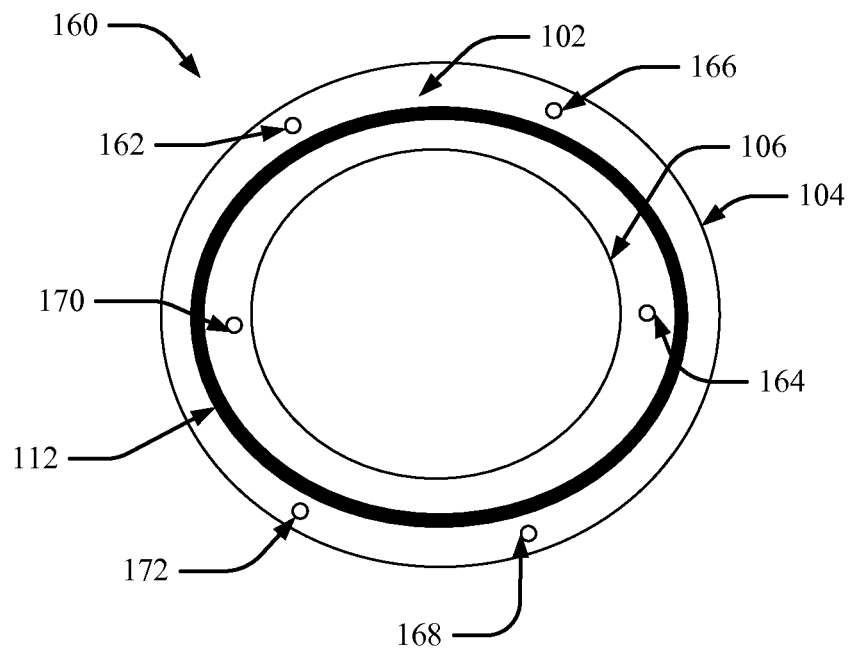
Figure 1G:
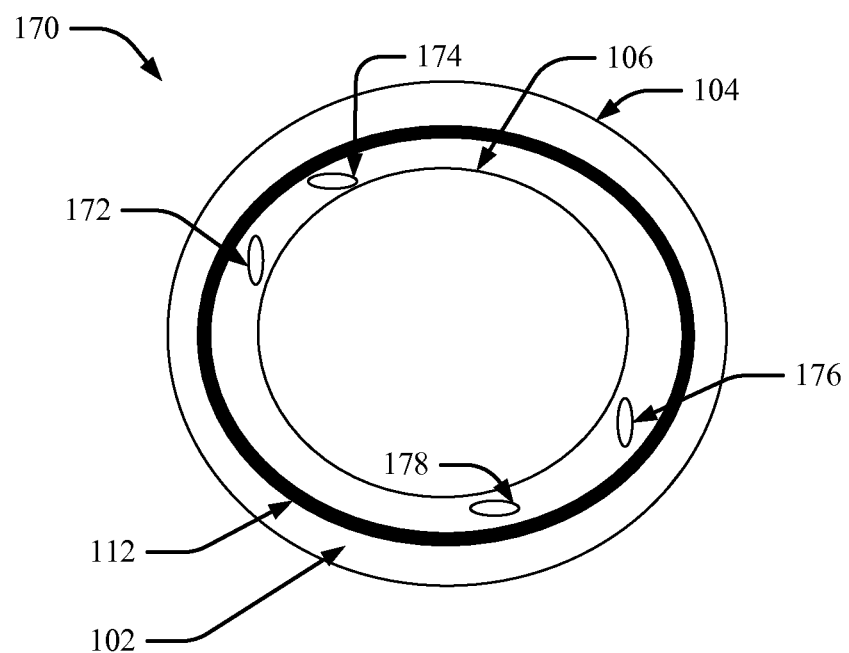

As shown in FIG. 1A, the indentations 108, 110 can be triangular-shaped. However, as shown in FIG. 1D, the indentations 142, 144 can be rounded. As another example, different configurations can be employed in the same contact lens. For example, as shown in FIG. 1E, indentations 108, 110 can be triangular-shaped and indentations 142, 144 can be rounded. Further, as shown in FIG. 1F, the indentations 162, 164, 166, 168, 170, 172 can be circular. As shown in FIG. 1G, the indentations 172, 174, 176, 178 can be slits. Any number of different and suitable configurations and/or shapes can be employed.

In various aspects, the configuration and/or positions of the indentations can be a function of the type of polymer layer 102. For example, a polymer layer 102 that is relatively thin (e.g., 5 nm) can have wrinkling more easily mitigated or avoided by the use of a first configuration of indentations (or by a particular set of positions of indentations).

In other aspects, a polymer layer 102 that is relatively thick (e.g., 200 nm) can have wrinkling more easily mitigated or avoided by the use of a second configuration of indentations (or a by another set of positions of indentations).

The indentations can be positioned in any number of suitable locations. For example, as shown in FIG. 1A, the indentations 108, 110 can be positioned on an inner edge 106 of the polymer layer 102. However, as shown in FIG. 1B, the indentations 122, 124 can be positioned on the outer edge 104 of the polymer layer 102. As shown in FIG. 1C, indentations can be positioned on the inner edge 106 and the outer edge 104 of the polymer layer 102 in some aspects. For example, indentations 122, 124 are on the outer edge 104 and indentations 108, 110 are on the inner edge 106.

The locations that are suitable for positioning of the indentations can be based on the size, type and/or shape of the metal portions disposed on or embedded within the polymer layer 102.

For example, if the metal portion is a size that is more than half the width of the polymer layer 102 ring, the indentations can be placed on a first edge (e.g., either the inner edge or the outer edge) of the ring. If the metal portions is a size that is less than half the width of the polymer layer 102 ring, the indentations can be placed on both the inner edge and the outer edge of the polymer layer 102 ring.

As another example, if the metal portion is substantially square or rectangular in shape, the indentations can be positioned such that the stress applied to the polymer layer 102 at the edges of the metal portion is reduced. For example, the indentations can be applied within a predefined distance to the edges of the metal portion.

As yet another example, if the type of the metal portion is such that a predefined amount of heat is generated by the metal portion leading to a high likelihood of wrinkling or tearing, the indentations in the region of the metal portion can be placed in positions associated with a direction from the metal portion in which the heat is dispersed.

As shown in FIGS. 1F and 1G, indentations can be disposed within the polymer layer 102 (as opposed to being disposed on an edge of the polymer layer 102). As such, the indentation can be encompassed by the polymer layer 102 on all sides of the indentation.

In various aspects, the indentations can be spaced at different positions relative to one another. For example, the indentations can be equally spaced from one another. In other example, the indentations can be spaced at randomly intervals within or along the polymer layer 102.

For example, in some aspects, the spacing between the positions of the indentations can be a function of the spacing between the metal portions on the polymer layer 102. By way of example, but not limitation, in aspects with equal spacing between the metal portions, the indentations can dispersed across the entirety of the polymer layer 102 equally spaced from one another. As another example, in aspects with unequal spacing between the metal portions (e.g., two metal portions on a first side of the polymer layer 102 ring and a third metal portion on the second side), the indentations can be spaced such that a greater number of indentations are provided on the side of the polymer layer 102 ring that has the greater number of metal portions.

As another example, the indentations can be in opposing directions. For example, as shown in FIG. 1E, the indentations 142, 144 have an open area that is formed in a direction away from the inner edge 106 of the polymer layer while the indentations 108, 110 have an open area that is formed in a direction toward the inner edge 106. As another example, the indentations can be staggered relative to one another.

Similar to that described above, the direction of the indentations can be a function of the thickness of the polymer layer 102 (e.g., in different locations, the polymer layer 102 can be different thicknesses, which can dictate the direction in which the indentation is placed). In some aspects, the direction of the indentations can be a function of the shape of the metal portion. For example, metal portions having square or rectangular shape can have nearby indentations having open areas that are faced towards the edge of the square or rectangular shape.

While the polymer layer 102 is shown in the form of a ring, in various aspects, the polymer layer 102 can be any number of different configurations including, but not limited to, circular, oval, square, rectangular or any number of polygons (including irregular polygons).

The contact lens 200 can also include a metal portion 112. The metal portion 112 can be attached to, disposed on and/or embedded within the substrate (not shown) and/or polymer layer 102. In various aspects, the metal portion 112 can include, but is not limited to, copper (Cu) or other biocompatible metals (or combinations thereof including, but not limited to, iron, titanium and/or nitinol.

While the metal portion 112 is shown in the form of a ring, in various aspects, the metal portion 112 can be any number of different configurations. In various embodiments, the metal portion 112 can be any number of different configurations that enable the metal portion 112 to have no portions extending beyond the polymer layer 102. For example, the metal portion 112 can be a square, rectangular, oval, circular or irregular polygonal shape. Additionally, in various aspects, the metal portion 112 can be contiguous or non-contiguous. By way of example, but not limitation, a first instance of the metal portion 112 on the polymer layer 102 can be provided for a circuit and a second instance of the metal portion on the 112 on the same polymer layer 102 can be provided for an antenna. The first and second instance can be non-contiguous.

In various aspects, the metal portion 112 can be electrically and/or communicatively coupled to one or more components (e.g., antenna, power supply, sensors, integrated circuit (or components thereof) or the like). For example, the components can be disposed on, coupled to and/or integrally formed with the metal portion 112. As examples, one or more of the antenna, power supply, sensors, integrated circuit or the like can be connected to the metal portion 112 via one or more electrical connections or integrally molded with the metal portion 112.

In various aspects, the polymer layer 102 and/or the metal portion 112 can be encapsulated by the substrate. In other aspects, in lieu of encapsulating the entirety of the polymer layer 102 and metal portion 112 in the substrate, only a single side of the polymer layer 102 and/or metal portion 112 can be covered in whole or in part by the substrate. For example, the side of the polymer layer 102 and/or metal portion 112 in contact with the eye can be covered in whole or in part by the substrate to shield the eye from the contact lens components (e.g., antenna, sensors, etc.).

Figure 2:
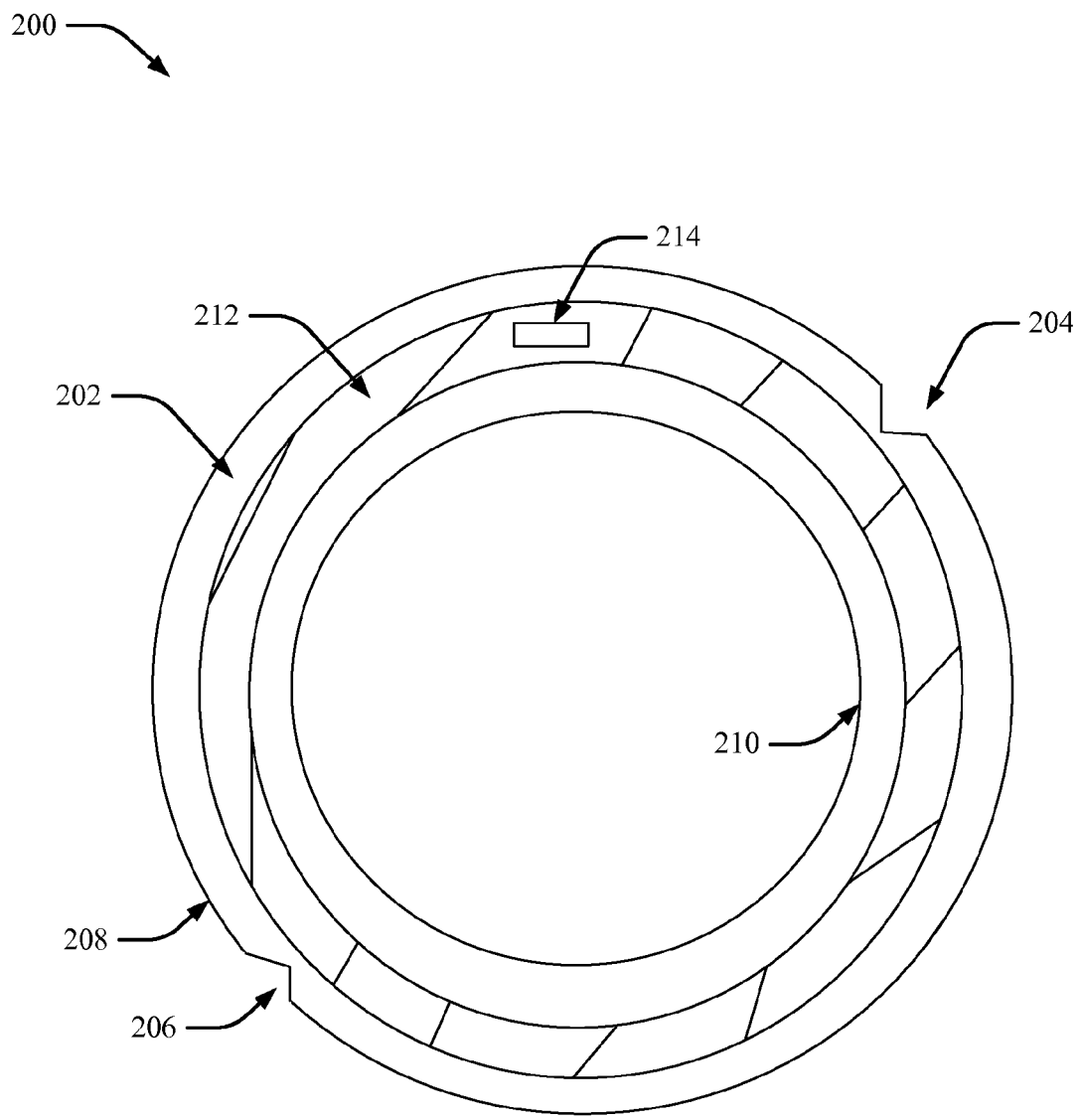
FIG. 2 is an illustration of a diagram of an exemplary non-limiting contact lens with a metal portion and attached polymer layer with indentations that reduce likelihood of wrinkling of the polymer layer in accordance with aspects described herein.

FIG. 2 is an illustration of block a diagram of an exemplary non-limiting contact lens with a metal portion and attached polymer layer with indentations that reduce a likelihood of wrinkling of the polymer layer in accordance with aspects described herein. The contact lens 200 can include a polymer layer 202 having one or more indentations 204, 206 on an outer edge 208 or inner edge 210 of the polymer layer 202. A metal portion 212 can be attached to or disposed within the polymer layer 202 and/or contact lens 200. In various aspects, one or more components 214 can be electrically and/or communicatively coupled to the metal portion 212. The components 214 can include, but are not limited to, an antenna, a power supply, a circuit or the like.

Figure 3:
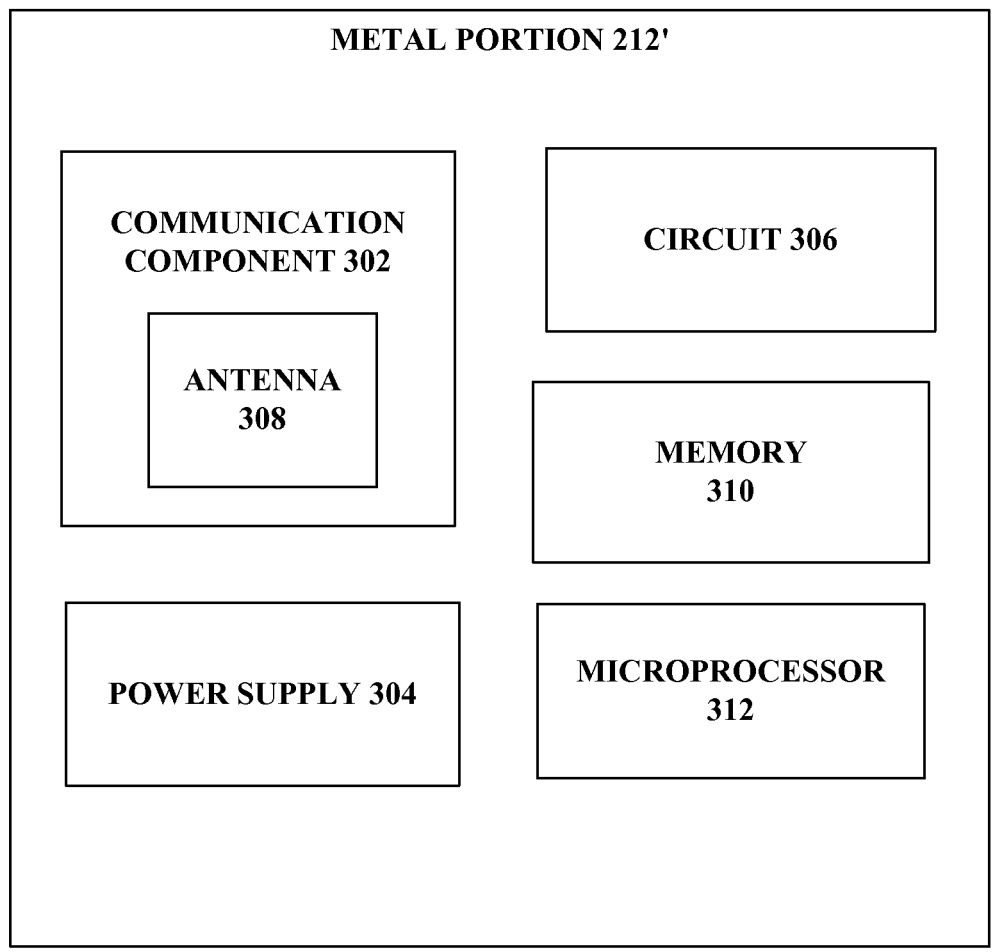
FIG. 3 is an illustration of a diagram of an exemplary non-limiting metal portion for a contact lens with a polymer layer in accordance with aspects described herein.

FIG. 3 is an illustration of a block diagram of an exemplary non-limiting metal portion for a contact lens with a polymer layer in accordance with aspects described herein. In some aspects, the metal portion 212' can include (or be electrically or communicatively coupled to) a communication component 302, power supply 304, circuit 306, an antenna 308, memory 310 and/or microprocessor 312. In some aspects, one or more of the communication component 302, power supply 304, circuit 306, antenna 308, memory 310 and/or microprocessor 312 can be electrically and/or communicatively coupled to one another (or to the metal portion 212') and/or integrally formed with one another (or the metal portion 212').

In some aspects, the metal portion 212' can be disposed on a polymer layer attached to or disposed within a contact lens. In some aspects, the metal portion 212' can be attached to or disposed within a substrate of the contact lens.

In various aspects, the metal portion 212' can be formed as metal portion 212 shown and described with reference to FIG. 2. Specifically, the metal portion 212' can be ring-shaped on the contact lens 200. In other aspects, the metal portion 212' can be any number of different shapes.

The communication component 302 can transmit and/or receive information to and/or from the contact lens (e.g., contact lens 100, 120, 130, 140, 150, 160, 170, 200). In some aspects, the communication component 302 can include antenna 308, which can transmit and/or receive information to and/or from the contact lens.

The power supply 304 can generate power and/or receive energy for generating power. For example, in some aspects, the power supply 304 can include one or more photovoltaic cells for generation of solar power. In various aspects, any number of other different types of power sources (e.g., electrical) can be implemented as the power supply 304. In some aspects, the power supply 304 can be or include a battery and/or a microelectromechanical system (MEMS) device. For example, in some embodiments, a MEMS device can serve as a power supply 304 by employing piezoelectric components that deform to generate power.

The circuit 306 can include one or more components for sensing, generating and/or processing information. For example, the circuit 306 can include one or more sensors for detection of a biological feature associated with the wearer of the contact lens or for detection of a chemical feature of an environment outside of the wearer of the contact lens. In various aspects, the biological and/or chemical features can include, but are not limited to, the level of glucose, lactate, hydrogen ions and/or urea in the body of the wearer of the contact lens.

In other aspects, the circuit 306 can include the microprocessor 312 for performing one or more functions. In some aspects, the circuit 306 can be an integrated circuit.

The memory 310 can be a computer-readable storage medium storing computer-executable instructions and/or information for performing the functions described in this disclosure with reference to the functions performed on or via the metal portion 212' or via one or more of the components coupled to the metal portion 212'. The microprocessor 312 can perform one or more of the functions described in this disclosure with reference to the functions performed on or via the metal portion 212' or via one or more of the components coupled to the metal portion 212'.

While the aspects herein describe the indentations of the polymer layer serving as stress relief cuts to reduce the likelihood that the polymer layer will wrinkle, in various aspects, the indentations can be provided for different purposes including medicine application, providing oxygen to the eye and the like.

While the aspects described herein describe the polymer layer in connection with the metal portion, in some aspects, the polymer layer can be incorporated into a substantially rigid corrective lens that can apply pressure to the cornea of the eye for correction of vision.

Figure 4:
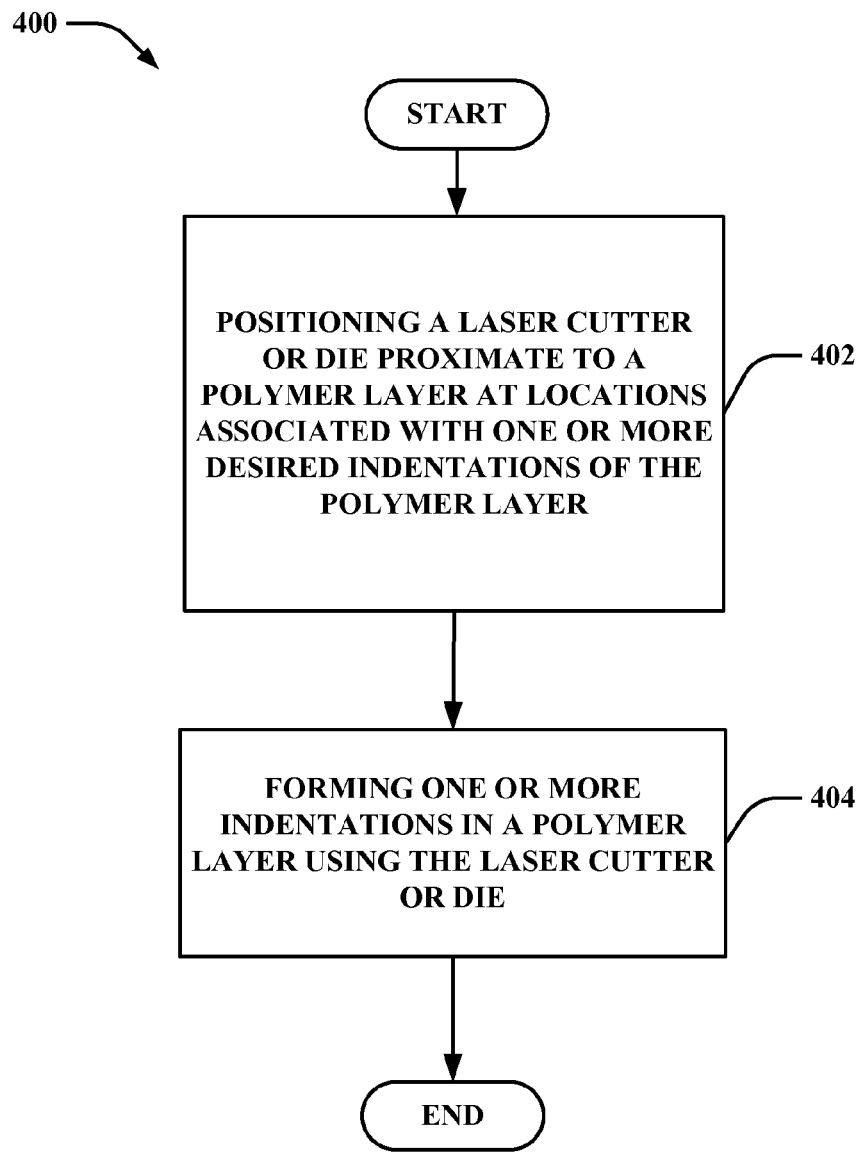
FIGS. 4 and 5 are illustrations of exemplary flow diagrams of methods of forming indentations in a polymer layer of a contact lens in accordance with aspects described herein.
Figure 5:
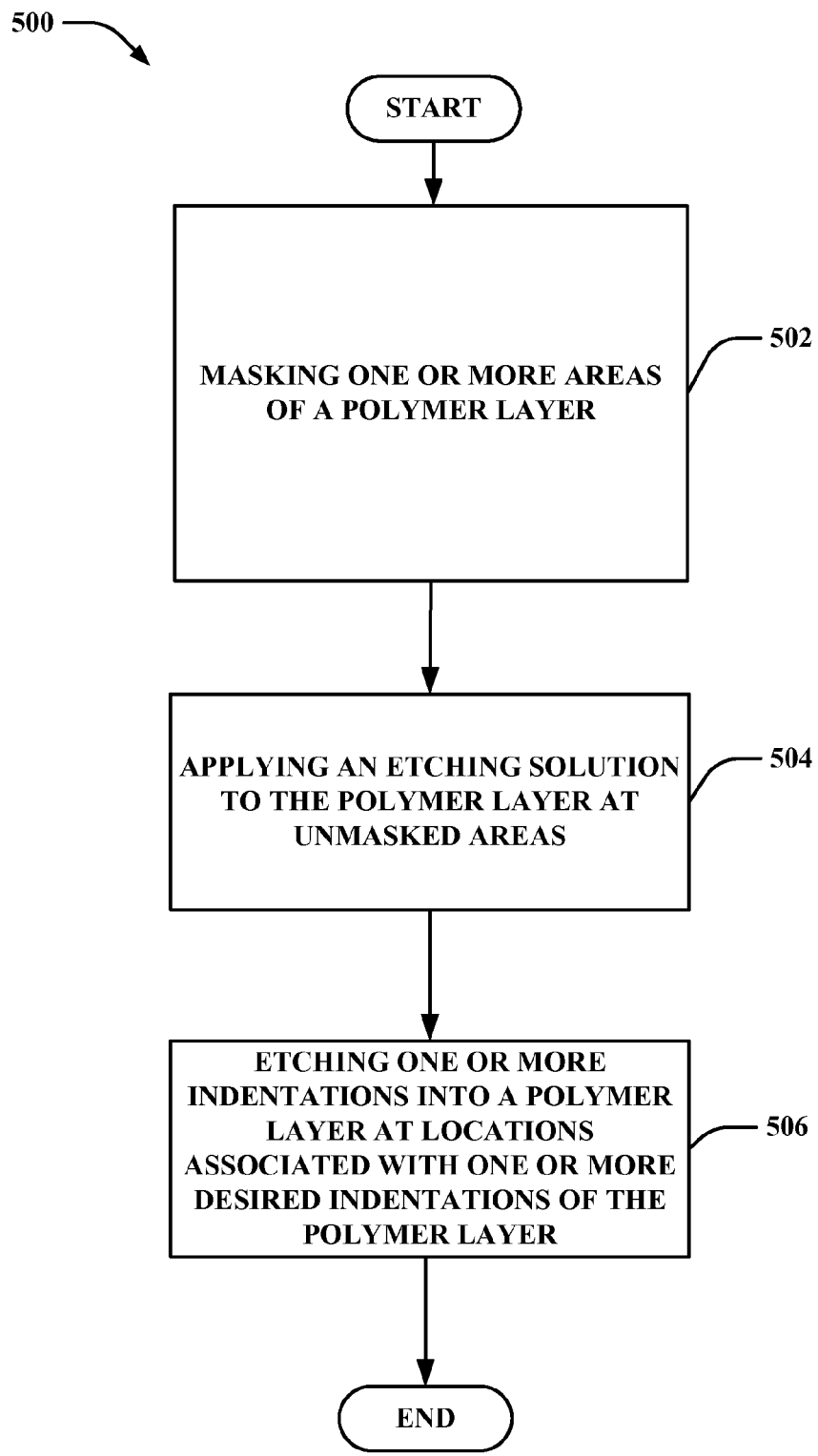

FIGS. 4 and 5 are illustrations of exemplary flow diagrams of methods of forming indentations in a polymer layer of a contact lens in accordance with aspects described herein.

Turning first to FIG. 4, at 402, method 400 can include positioning a laser cutter or die proximate to a polymer layer at locations associated with one or more desired indentations of the polymer layer. For example, the laser cutter or die can be applied at an outer edge of the polymer layer for creating indentations on the outer edge of the polymer layer. As another example, the laser cutter or die can be applied at the center region of the polymer layer for creating a polymer layer ring wherein the ring is centered within the polymer layer.

At 404, method 400 can include forming one or more indentations in a polymer layer using the laser cutter or die. In various aspects, the indentations can be formed by the application of the laser to the polymer layer (or, in the case of the die, by the application of the die to the polymer layer).

Turning now to FIG. 5, at 502, method 500 can include masking one or more areas of a polymer layer. The masking can be performed using a metal mask placed over the polymer layer in some aspects. The mask can be shaped and sized in a manner such that various regions of the polymer layer are uncovered when the mask is placed above the polymer layer. The regions that are uncovered can be those that will be removed to create the indentations (or to create the polymer layer ring).

At 504, method 500 can include applying an etching solution to the polymer layer at unmasked areas. In various aspects, the etching solution can be or include plasma. At 506, method 500 can include etching one or more indentations into a polymer layer at locations associated with one or more desired indentations of the polymer layer. The etching process can be the reactive ion etching process in some embodiments.

Figure 6:
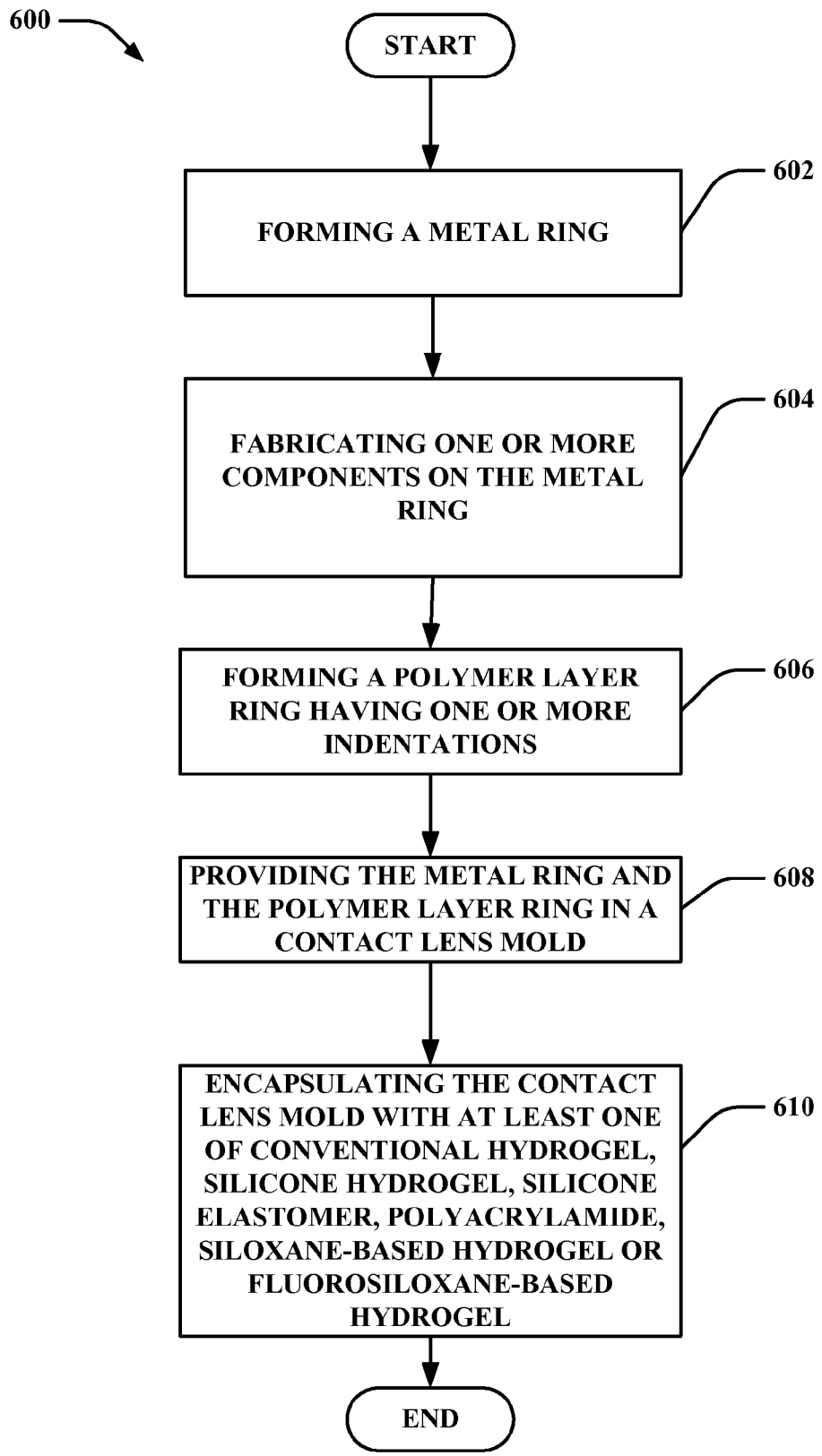
FIG. 6 is an illustration of an exemplary flow diagram of a method of manufacturing a contact lens having a polymer layer with one or more indentations in accordance with aspects described herein.

FIG. 6 is an illustration of an exemplary flow diagram of a method of manufacturing a contact lens having a polymer layer with one or more indentations in accordance with aspects described herein.

At 602, method 600 can include forming a metal ring. In various aspects, the metal ring can be formed by piercing the center of a sheet of metal. The sheet of metal can be pierced by a metal die formed in the shape of a ring, for example. At 604, method 600 can include fabricating one or more components on the metal ring. In various aspects, the components can include an antenna, sensor, circuit and/or power supply.

At 606, method 600 can include forming a polymer layer ring having one or more indentations. In various aspects, the indentations and/or ring can be formed by removing portions of the polymer layer via an etching process. For example, reactive ion etching can be performed by applying plasma to the polymer layer. In other aspects, the indentations and/or ring can be formed by removing portions of the polymer layer via laser cutting the portions away from the polymer layer. In other aspects, the indentations and/or ring can be formed by removing portions of the polymer layer by applying a metal die in the shape of the ring or being shaped in a manner corresponding to the desired shape and location of the indentations of the polymer layer At 608, method 600 can include providing the metal ring and the polymer layer ring in a contact lens mold. In some aspects, the metal ring and polymer layer ring can be formed in a curved shape corresponding to the contact lens mold prior to placing the metal ring and polymer layer ring in the contact lens mold. In some aspects, heat and/or pressure can be applied to join the metal ring and the polymer layer ring. Accordingly, the indentations in the polymer layer ring can minimize wrinkling typically that typically results from bending a polymer material or applying heat and/or pressure to a polymer material.

At 610, method 600 can include encapsulating the contact lens mold with at least one of conventional hydrogel, silicone hydrogel, silicone elastomer, polyacrylamide, siloxane-based hydrogel or fluorosiloxane-based hydrogel. In various aspects, the contact lens mold can be encapsulated in other different types of material (other than the above-mentioned materials). For example, for hard contact lenses, the contact lens mold can be encapsulated in polymethyl methacrylate (PMMA), silicone acrylate or fluoro-silicone acrylate.

Exemplary Networked and Distributed Environments

Figure 7:
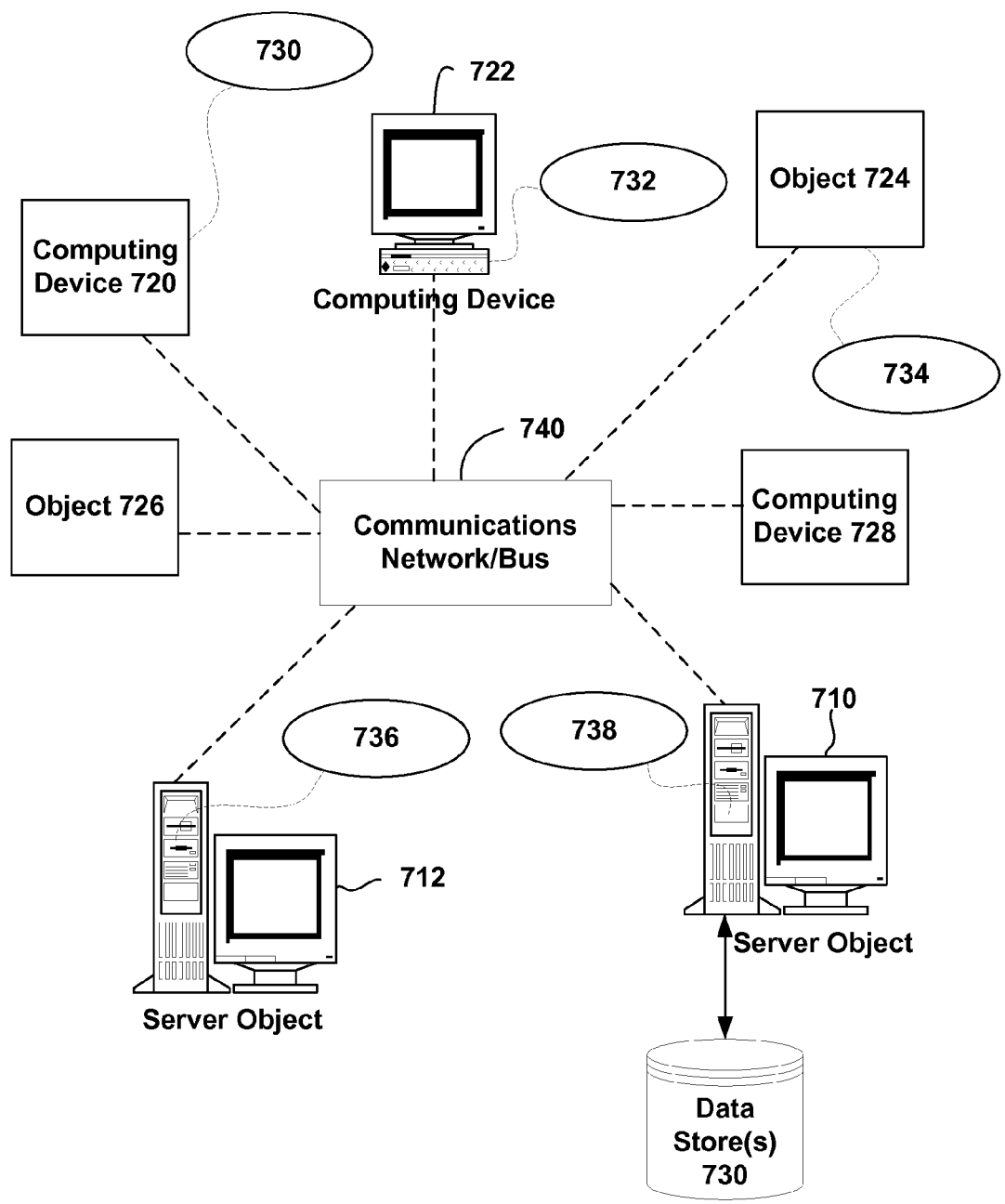
FIG. 7 is an illustration of a schematic diagram of an exemplary networked or distributed computing environment with which one or more aspects described herein can be associated.

FIG. 7 provides a schematic diagram of an exemplary networked or distributed computing environment with which one or more aspects described in this disclosure can be associated. The distributed computing environment includes computing objects 710, 712, etc. and computing objects or devices 720, 722, 724, 726, 728, etc., which can include programs, methods, data stores, programmable logic, etc., as represented by applications 730, 732, 734, 736, 738. It can be appreciated that computing objects 710, 712, etc. and computing objects or devices 720, 722, 724, 726, 728, etc. can include different devices, such as active contact lenses (and components thereof), personal digital assistants (PDAs), audio/video devices, mobile phones, MPEG-1 Audio Layer 3 (MP3) players, personal computers, laptops, tablets, etc.

Each computing object 710, 712, etc. and computing objects or devices 720, 722, 724, 726, 728, etc. can communicate with one or more other computing objects 710, 712, etc. and computing objects or devices 720, 722, 724, 526, 528, etc. by way of the communications network 740, either directly or indirectly. Even though illustrated as a single element in FIG. 7, network 740 can include other computing objects and computing devices that provide services to the system of FIG. 7, and/or can represent multiple interconnected networks, which are not shown.

In a network environment in which the communications network/bus 740 can be the Internet, the computing objects 710, 712, etc. can be Web servers, file servers, media servers, etc. with which the client computing objects or devices 720, 722, 724, 726, 728, etc. communicate via any of a number of known protocols, such as the hypertext transfer protocol (HTTP).

Exemplary Computing Device

As mentioned, advantageously, the techniques described in this disclosure can be associated with any suitable device. It is to be understood, therefore, that handheld, portable and other computing devices (including active contact lens having circuitry or components that compute and/or perform various functions). As described, in some aspects, the device can be the contact lens (or components of the contact lens) described herein. In various aspects, the data store can include or be included within, any of the memory described herein, any of the contact lenses described herein. In various aspects, the data store can be any repository for storing information transmitted to or received from the contact lens.

Figure 8:
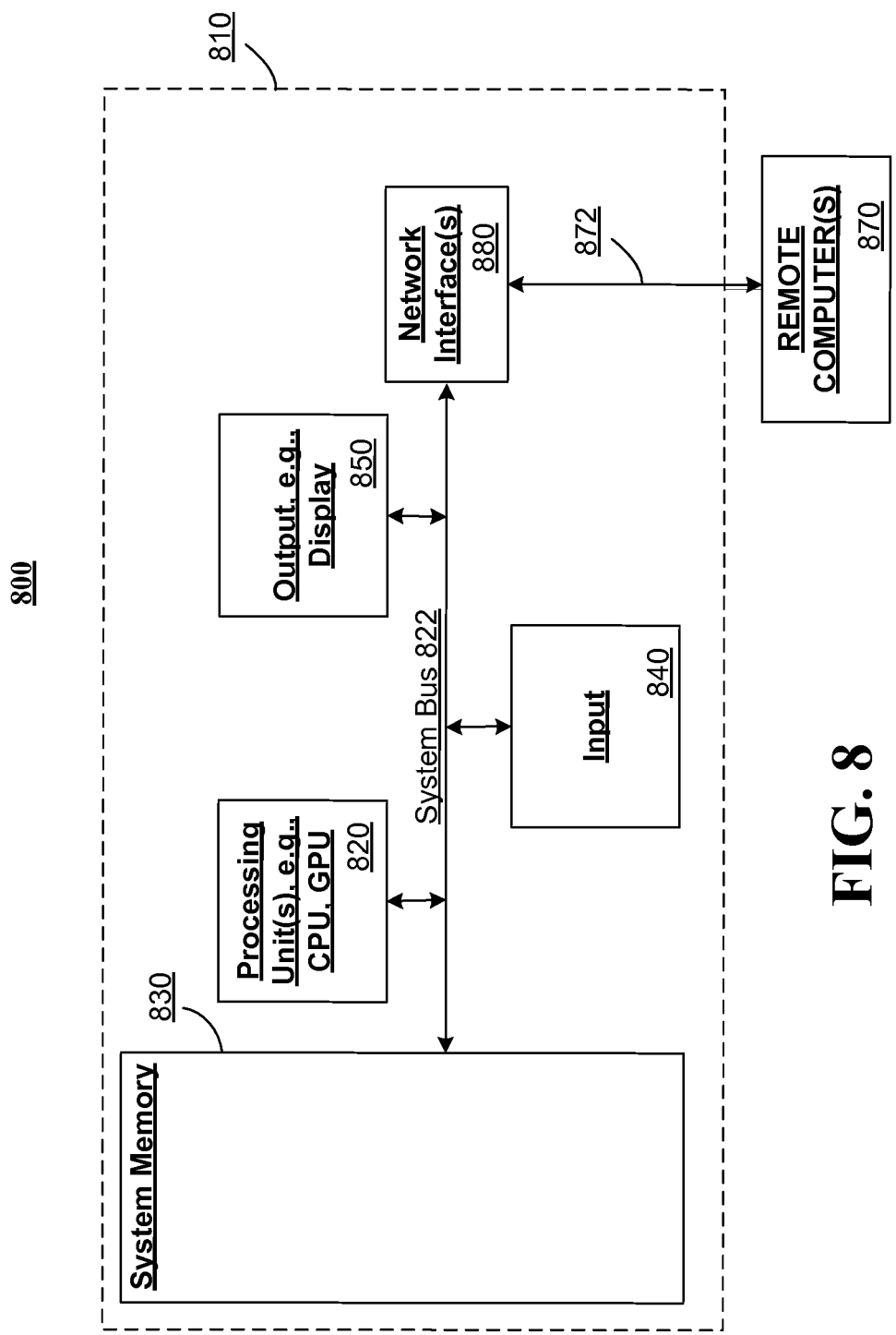
FIG. 8 is an illustration of a schematic diagram of an exemplary computing environment with which one or more aspects described herein can be associated.

FIG. 8 illustrates an example of a suitable computing system environment 800 in which one or aspects of the aspects described in this disclosure can be implemented. Components of computer 810 can include, but are not limited to, a processing unit 820, a system memory 830, and a system bus 822 that couples various system components including the system memory to the processing unit 820.

Computer 810 typically includes a variety of computer readable media and can be any available media that can be accessed by computer 810. The system memory 830 can include computer storage media in the form of volatile and/or nonvolatile memory such as read only memory (ROM) and/or random access memory (RAM). By way of example, and not limitation, memory 830 can also include an operating system, application programs, other program components, and program data.

A user can enter commands and information into the computer 810 through input devices 840 (e.g., keyboard, keypad, a pointing device, a mouse, stylus, touchpad, touch screen, motion detector, camera, microphone or any other device that allows the user to interact with the computer 810). A monitor or other type of display device can be also connected to the system bus 822 via an interface, such as output interface 850. In addition to a monitor, computers can also include other peripheral output devices such as speakers and a printer, which can be connected through output interface 850.

The computer 810 can operate in a networked or distributed environment using logical connections to one or more other remote computers, such as remote computer 880. The remote computer 880 can be a personal computer, a server, a router, a network PC, a peer device or other common network node, or any other remote media consumption or transmission device, and can include any or all of the elements described above relative to the computer 810. The logical connections depicted in FIG. 8 include a network 882, such local area network (LAN) or a wide area network (WAN), but can also include other networks/buses e.g., cellular networks.

Computing devices typically include a variety of media, which can include computer-readable storage media and/or communications media, in which these two terms are used herein differently from one another as follows. Computer-readable storage media can be any available storage media that can be accessed by the computer, can be typically of a non-transitory nature, and can include both volatile and nonvolatile media, removable and non-removable media. By way of example, and not limitation, computer-readable storage media can be implemented in connection with any method or technology for storage of information such as computer-readable instructions, program components, structured data, or unstructured data. Computer-readable storage media can include, but are not limited to, RAM, ROM, electrically erasable programmable read only memory (EEPROM), flash memory or other memory technology, or other tangible and/or non-transitory media which can be used to store desired information. Computer-readable storage media can be accessed by one or more local or remote computing devices, e.g., via access requests, queries or other data retrieval protocols, for a variety of operations with respect to the information stored by the medium. In various aspects, the computer-readable storage media can be, or be included within, the memory or contact lens (or components thereof) described herein.

On the other hand, communications media typically embody computer-readable instructions, data structures, program components or other structured or unstructured data in a data signal such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals.

It is to be understood that the aspects described in this disclosure can be implemented in hardware, software, firmware, middleware, microcode, or any combination thereof. For a hardware aspect, the processing units can be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors and/or other electronic units designed to perform the functions described in this disclosure, or a combination thereof.

For a software aspect, the techniques described in this disclosure can be implemented with components or components (e.g., procedures, functions, and so on) that perform the functions described in this disclosure. The software codes can be stored in memory units and executed by processors.

What has been described above includes examples of one or more aspects. It is, of course, not possible to describe every conceivable combination of components or methodologies for purposes of describing the aforementioned aspects, but one of ordinary skill in the art can recognize that many further combinations and permutations of various aspects are possible. Accordingly, the described aspects are intended to embrace all such alterations, modifications and variations that fall within the spirit and scope of the appended claims.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

The aforementioned systems have been described with respect to interaction between several components. It can be appreciated that such systems and components can include those components or specified sub-components. Sub-components can also be implemented as components communicatively coupled to other components rather than included within parent components (hierarchical). Additionally, it is to be noted that one or more components can be combined into a single component providing aggregate functionality. Any components described in this disclosure can also interact with one or more other components not specifically described in this disclosure but generally known by those of skill in the art.

In view of the exemplary systems described above methodologies that can be implemented in accordance with the described subject matter will be better appreciated with reference to the flowcharts of the various figures. While for purposes of simplicity of explanation, the methodologies are shown and described as a series of blocks, it is to be understood and appreciated that the claimed subject matter is not limited by the order of the blocks, as some blocks can occur in different orders and/or concurrently with other blocks from what is depicted and described in this disclosure. Where non-sequential, or branched, flow is illustrated via flowchart, it can be appreciated that various other branches, flow paths, and orders of the blocks, can be implemented which achieve the same or a similar result. Moreover, not all illustrated blocks may be required to implement the methodologies described in this disclosure after.

In addition to the various aspects described in this disclosure, it is to be understood that other similar aspects can be used or modifications and additions can be made to the described aspect(s) for performing the same or equivalent function of the corresponding aspect(s) without deviating there from. Still further, multiple processing chips or multiple devices can share the performance of one or more functions described in this disclosure, and similarly, storage can be provided across a plurality of devices. The invention is not to be limited to any single aspect, but rather can be construed in breadth, spirit and scope in accordance with the appended claims.

What is claimed is:

1. A contact lens, comprising:
   a ring-shaped polymer layer, wherein the ring-shaped polymer layer has an inner edge defining an inner circumference and an outer edge defining an outer circumference, and wherein the ring-shaped polymer layer has one or more indentations on at least one of the inner edge or the outer edge;
   a metal portion disposed on the ring-shaped polymer layer between the inner edge and the outer edge; and
   a substrate, wherein the substrate encapsulates the metal portion and the ring-shaped polymer layer.

2. The contact lens of claim 1, wherein the metal portion is associated with an integrated circuit.

3. The contact lens of claim 1, wherein the metal portion is part of at least one of a conductor, a power supply, an antenna or a circuit.

4. The contact lens of claim 3, wherein the circuit comprises one or more sensors that detect a biological feature of a wearer of the contact lens.

5. The contact lens of claim 4, wherein the biological feature comprises a level of at least one of glucose, urea or lactate.

6. The contact lens of claim 1, wherein the one or more indentations have at least one of a triangular shape or a round shape.

7. The contact lens of claim 1, wherein the metal portion is ring shaped.

8. The contact lens of claim 1, wherein the one or more indentations comprise two or more indentations equally spaced from one another on at least one of the inner edge or the outer edge of the ring-shaped polymer layer.

9. The contact lens of claim 1, wherein the one or more indentations comprise a first set of one or more indentations on the inner edge of the ring-shaped polymer layer and a second set of one or more indentations on the outer edge of the ring-shaped polymer layer, wherein one or more indentations associated with the first set of one or more indentations are in an opposing direction from one or more indentations of the second set of one or more indentations.

10. The contact lens of claim 9, wherein locations of the first set of one or more indentations are staggered relative to locations of the second set of one or more indentations.

11. The contact lens of claim 1, wherein the one or more indentations are at least one of slits or circular in shape.

\* \* \* \* \*